United States Patent [19]

Kirby et al.

[11] 3,986,860
[45] Oct. 19, 1976

[54] CYCLIC ACETALS OF ALPHA-OXOCARBOXYLIC ACID DERIVATIVES

[75] Inventors: Peter Kirby, Maidstone; Eirlys R. Isaac, Sittingbourne, both of England

[73] Assignee: Shell Oil Company, Houston, Tex.

[22] Filed: Nov. 8, 1974

[21] Appl. No.: 522,078

Related U.S. Application Data

[62] Division of Ser. No. 254,536, May 18, 1972, Pat. No. 3,862,959.

[30] Foreign Application Priority Data

May 27, 1971  United Kingdom............... 17564/71

[52] U.S. Cl. .................................................. 71/88
[51] Int. Cl.² .......................................... P01N 9/28
[58] Field of Search ........................................ 71/88

[56] References Cited
UNITED STATES PATENTS

| | | | |
|---|---|---|---|
| 3,344,148 | 9/1967 | Dietrich et al. | 71/88 X |
| 3,427,147 | 2/1969 | Dietrich et al. | 71/88 |
| 3,555,045 | 1/1971 | Griffith et al. | 71/88 X |
| 3,644,422 | 2/1972 | Mine et al. | 71/88 X |
| 3,864,115 | 2/1975 | Schrader et al. | 71/88 |

Primary Examiner—Lewis Gotts
Assistant Examiner—Catherine L. Mills

[57]  ABSTRACT

Cyclic acetals of the formula

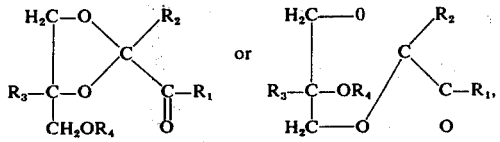

where $R_1$ is hydroxy, alkoxy, or NHZ, Z is hydrogen, alkyl, cycloalkyl, benzyl, or optionally substituted phenyl, $R_2$ is hydrogen or alkyl, $R_3$ is alkyl, and $R_4$ is aralkyl, are useful as herbicides.

8 Claims, No Drawings

CYCLIC ACETALS OF ALPHA-OXOCARBOXYLIC ACID DERIVATIVES

This is a division of application Ser. No. 254,536, filed May 18, 1972, now U.S. Pat. No. 3,862,959, issued Jan. 28, 1975.

BACKGROUND OF THE INVENTION

1. Field of the Invention

This invention relates to a novel class of cyclic acetals of alpha-oxocarboxylic acid derivatives, to herbicidal compositions containing them, and to their use as herbicides.

2. Description of the Prior Art

A search of the prior art indicates the herbicidal cyclic acetals within the scope of this invention to be novel.

Summary of the Invention

It has now been found that certain novel cyclic acetals of alpha-oxocarboxylic acid derivatives exhibit high herbicidal activity in the control of certain economically important grass weed species.

DESCRIPTION OF THE PREFERRED EMBODIMENTS

The present invention relates to cyclic acetals having one or the other of the following isomeric formulae:

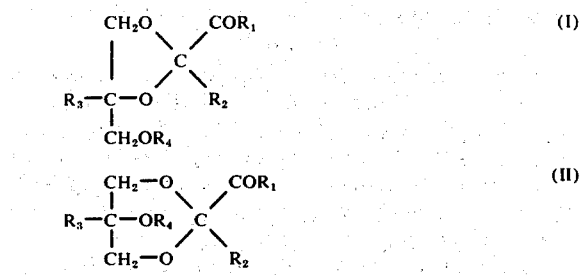

where $R_1$ is hydroxy or alkoxy or a group of formula:

—NHZ in which Z is hydrogen, alkyl, cycloalkyl or benzyl, phenyl-substituted amino, or phenyl optionally substituted by one or more halogen, alkyl, or alkoxy groups; $R_2$ is hydrogen or alkyl; $R_3$ is alkyl; and $R_4$ is aralkyl.

Preferred cyclic acetal derivatives are (a) those of formula I where $R_1$ is hydroxy, alkoxy of 1–6 carbon atoms, for example ethoxy, or a group of formula:
—NHZ in which Z is a hydrogen atom, alkyl or cycloalkyl up to 6 carbon atoms, for example butyl or cyclohexyl, benzyl, phenylamino, or phenyl optionally substituted by a fluorine atom, by one or two chlorine atoms, by one or two alkyl groups of 1–6 carbon atoms, for example methyl, or by an alkoxy group of 1–6 carbon atoms, for example methoxy; $R_2$ is hydrogen or alkyl of 1–6 carbon atoms, for example methyl; $R_3$ is alkyl of 1–6 carbon atoms, for example methyl, ethyl or propyl, and $R_4$ is benzyl, or (b) those of formula II where $R_1$ is hydroxy, alkoxy of 1–6 carbon atoms, for example ethoxy, or a group of formula:

—NHZ in which Z is hydrogen or phenyl; $R_1$ and $R_2$ each independently is alkyl of 1–6 carbon atoms, for example methyl; and $R_4$ is benzyl.

Particularly herbicidally active compounds of this invention (a) those of formula I where $R_1$ is hydroxy, ethoxy, or a group of formula —NHZ, in which Z is hydrogen, butyl, cyclohexyl, benzyl, phenylamino, fluorophenyl, chlorophenyl, dichlorophenyl, tolyl, dimethylphenyl, or methoxyphenyl; $R_2$ is hydrogen or methyl; $R_3$ is methyl, ethyl, or propyl; and $R_4$ is benzyl, or (b) those of formula II where $R_1$ is hydroxy, ethoxy, or a group of formula —NHZ, where Z is hydrogen or phenyl; $R_2$ and $R_3$ are each methyl; and $R_4$ is benzyl.

A particularly preferred class of compounds, having a high degree of herbicidal activity, are those of formula I where $R_1$ is phenylamino and $R_2$ is methyl.

Those derivatives of formula I or II where $R_1$ is alkoxy are prepared by a process which comprises reacting an alkyl ester of an α-oxocarboxylic acid, or non-cyclic acetal thereof, with the appropriate substituted propane diol, in the presence of an anhydrous acid catalyst, for example hydrogen chloride or boron trifluoride.

The derivatives where $R_1$ is hydroxy are prepared by saponification of the derivative where $R_1$ is alkoxy, using, for example, a strong base such as sodium hydroxide and liberating the acid from the salt so obtained by treatment with a mineral acid, such as hydrochloric acid.

The compounds where $R_1$ is a group of formula:

—NHZ are obtained by reacting the corresponding compound where $R_1$ is alkoxy or acyloxy, for example alkoxycarbonyloxy, with a compound of formula:

$NH_2Z$ .

When $R_1$ is phenyl-substituted amino the compound is conveniently obtained by reacting the corresponding compound where $R_1$ is hydroxy with phenyl-phosphazoanilide.

The cyclic acetal derivatives of the invention are of interest as broad spectrum herbicides particularly against grass weed species. The invention includes therefore herbicidal compositions comprising a carrier or a surface-active agent, or both a carrier and a surface-active agent, and, as active ingredient, at least one cyclic acetal derivative of formula I or II. Likewise the invention includes also a method of combating weeds at a locus which comprises applying to the locus a herbicidally effective amount of a cyclic acetal or composition of the invention.

The term "carrier as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example kaolinites, montmorillonites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent and, where necessary, 0–10% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½ – 10% by weight of toxicant. Granules are usually prepared to have a size between 10 and 100 BS mesh (1.676 – 0.152 mm), and may be manufactured by agglomeration or impregnation techniques. Generally granules will contain ½ – 25% by weight toxicant and 0 – 10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5 –15% W of dispersing agents, 0.1 – 10% w of suspending agents such as protective colloids and thixotropic agents, 0 – 10% w of appropriate additives such as defoamers, corrosion inhibitors, stabilisers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise-like' consistency.

The composition of the invention may also contain other ingredients, for example, other compounds possessing pesticidal, especially insecticidal, acaricidal, herbicidal or fungicidal, properties.

The invention is further illustrated in the following examples.

In the examples below, the structure of all the products prepared was confirmed by elemental analysis.

EXAMPLE 1

Ethyl 4-benzyloxymethyl-2,4-dimethyl-1,3-dioxolan-2-carboxylate

Dry hydrogen chloride gas was passed into a mixture of 3-benzyloxy-2-methylpropane-1,2-diol (14.9 grams) and ethyl pyruvate (9.15 grams) for 1 hour. The mixture was heated at 90° C for a further 1 hour and then cooled to 50° C. Benzene (100 milliliters) was added to the mixture and the water formed in the reaction was removed azeotropically. The cooled solution was washed with potassium carbonate solution and dried. The solvent was removed under reduced pressure and the residue was fractionally distilled to yield the desired product boiling point 124–126° C at 0.3 Torr.

EXAMPLE 2

4-Benzyloxymethyl-2,4-dimethyl-1,3-dioxolan-2-carboxylic acid

Ethyl 4-benzyloxymethyl-2,4-dimethyl-1,3-dioxolan-2-carboxylate (7.0 grams, prepared as in Example 1) was stirred with a solution of sodium hydroxide (1.0 gram) in water (50 milliliters) at 90° C for 4 hours. The alcohol formed was removed under reduced pressure. The aqueous residue was washed twice with ether and acidified with 2M hydrochloric acid (10 milliliters). The mixture was extracted with ether and the extracts were washed, dried (MgSO$_4$) and evaporated under reduced pressure. The residue was fractionally distilled to give the desired product boiling point 145° C at 0.1 Torr.

EXAMPLE 3

4-Benzyloxymethyl-2,4-dimethyl-1,3-dioxolan-2-(N-phenylcarboxamide)

4-Benzyloxymethyl-2,4-dimethyl-1,3-dioxolane-2-carboxylic acid (3.0 grams, prepared as in Example 2) and phenyl phosphazoanilide (1.13 grams, prepared by the reaction of phosphorus trichloride with aniline) in toluene (25 milliliters) were heated together under reflux for 2 hours. The mixture was filtered and the residue was washed with hot toluene. The toluene was removed under reduced pressure and the residue was taken up in chloroform. The solution was shaken with 5% aqueous sodium bicarbonate solution and then with water and dried (MgSO$_4$). The solvent was removed under reduced pressure and the residue purified by chromatography on silica gel using chloroform as eluant to give the desired product melting point 53°–60° C. (isomer mixture).

EXAMPLE 4

4-Benzyloxymethyl-2,4-dimethyl-1,3-dioxolan-2-carboxamide

Ethyl 4-benzyloxymethyl-2,4-dimethyl-1,3-dioxolan-2-carboxylate (5.0 grams) and concentrated aqueous ammonia solution (50 milliliters, 0.880 S.G.) were stirred together at room temperature for 3 days. The white solid formed was filtered off, washed with water and recrystallised from cyclohexane to give the desired product as an isomer mixture melting point 72°–92° C.

EXAMPLE 5

4-Benzyloxymethyl-2,4-dimethyl-1,3-dioxolan-2-(N-butylcarboxamide)

Triethylamine (3.2 grams) was added to a solution of 4-benzyloxymethyl-2,4-dimethyl-1,3-dioxolan-2-carboxylic acid (8.0 grams) in dry tetrahydrofuran (50 milliliters) maintained at 0°–5° C. The mixture was stirred for 10 minutes and isobutyl chloroformate (4.1 grams) was added while the temperature of the mixture was maintained at 5°–10° C. The stirring was continued for a further 20 minutes. Butylamine (2.2 grams) was then added and the mixture stirred for 16 hours at room temperature. The mixture was then filtered and the filtrate was evaporated under reduced pressure. The residue was dissolved in ether and the solution was washed in turn with 2M hydrochloric acid, 5% sodium bicarbonate solution and water. The solution was then dried and the solvent was removed under reduced pressure. The residue was purified by chromatography on silica gel using chloroform as eluant to give the desired product as an oil R$_f$(CHCl$_3$) 0.2.

EXAMPLE 6

Ethyl 4-benzyloxymethyl-4-methyl-1,3-dioxolan-2-carboxylate

3-Benzyloxy-2-methylpropane-1,2-diol (19.6 grams), ethyl diethoxyacetate (17.6 grams) and boron trifluoride etherate (2 milliliters) were heated together with stirring in a distillation apparatus. Heating was continued until ca 9.0 grams ethanol had been collected. Chloroform (100 milliliters) was added to the cooled residue and the solution obtained was washed first with 5% aqueous potassium carbonate solution and then with water. The solution was dried (MgSO$_4$) and the solvent was removed under reduced pressure. The residue was purified by fractional distillation followed by chromatography on silica gel eluting with toluene and then 5% ether in toluene. The desired product was obtained as an oil R$_f$(CHCl$_3$) 0.39.

EXAMPLE 7

Following procedures analogous to those of the previous examples further compounds were prepared, whose physical characteristics and analyses are set out in Table 1. The R$_f$ values given for certain of the compounds were obtained by thin layer chromatography on coated silica gel plates (5×10 cm) with a layer thickness 0.25 mm using the solvents indicated. In certain cases where a mixture of geometrical isomers was obtained the individual isomers were separated by fractional crystallization.

TABLE 1

| Compound | Melting Point or Boiling Point ° C. or R$_f$(solvent) |
| --- | --- |
| 5-benzyloxy-2,5-dimethyl-1,3-dioxane-2-(N-phenyl-carboxamide) (isomer mixture) | melting point 55 – 70 |
| ethyl 5-benzyloxy-2,5-dimethyl-1,3-dioxane-2-carboxylate | boiling point 138 at 0.2mm Hg |
| 5-benzyloxy-2,5-dimethyl-1,3-dioxane-2-carboxamide | melting point 122 – 125 |
| 5-benzyloxy-2,5-dimethyl-1,3-dioxane-2-carboxylic acid | R$_f$(2.5% ether/CHCl$_3$) 0.095 |
| N-((4-benzyloxymethyl-2,4-dimethyl-1,3-dioxolane-2-yl)carbonyl)-N'-phenylhydrazide | R$_f$ (CHCl$_3$) 0.36 |
| 4-benzyloxymethyl-2,4-dimethyl-1,3-dioxolane-2-(N-cyclohexylcarboxamide) (isomer mixture) | melting point 64 – 90 |
| 4-benzyloxymethyl-2,4-dimethyl-1,3-dioxolane-2-(N-2,4-dichlorophenyl)carboxamide) | melting point 104 – 109 |
| 4-benzyloxymethyl-2,4-dimethyl-1,3-dioxolane-2-(N-(2,4-dimethylphenyl)carboxamide) | melting point 64 – 69 |
| ethyl 4-benzyloxymethyl-4-ethyl-2-methyl-1,3-dioxolane-2-carboxylate | boiling point 134 at 0.4mm Hg |
| 4-benzyloxymethyl-2,4-dimethyl-1,3-dioxolane-2-(N-benzylcarboxamide) | R$_f$ (CHCl$_3$) 0.53 |
| 4-benzyloxymethyl-4-ethyl-2-methyl-1,3-dioxolane-2-carboxylic acid | boiling point 156 at 0.2mm Hg |
| 4-benzyloxymethyl-4-ethyl-2-methyl-1,3-dioxolane-2-(N-phenylcarboxamide) (isomer 1) | melting point 102 – 106 |
| 4-benzyloxymethyl-4-ethyl-2-methyl-1,3-dioxolane-2-(N-phenylcarboxamide) (isomer 2) | melting point 65 – 67 |
| ethyl 4-benzyloxymethyl-2-methyl-4-propyl-1,3-dioxolane-2-carboxylate | boiling point 132 at 0.1 mm Hg |
| 4-benzyloxymethyl-2-methyl-4-propyl-1,3-dioxolane-2-carboxylic acid | R$_f$(2.5% ether/CHCL$_3$) |

TABLE 1-continued

| Compound | Melting Point or Boiling Point °C. or R$_f$(solvent) |
|---|---|
| | 0.26 ⎱ two isomers |
| | 0.14 ⎰ |
| 4-benzyloxymethyl-2-methyl-4-propyl-1,3-dioxolane-2-(N-phenylcarboxamide) (isomer 1) | melting point 97 – 99 |
| 4-benzyloxymethyl-2-methyl-4-propyl-1,3-dioxolane-2-(N-phenylcarboxamide) (isomer 2) | melting point 55 – 59 |
| 4-benzyloxymethyl-2-methyl-4-propyl-1,3-dioxolane-2-(N-benzylcarboxamide) | R$_f$ (CHCl$_3$) 0.55 |
| 4-benzyloxymethyl-2,4-dimethyl-1,3-dioxolane-2-(N-(4-chlorophenyl)carboxamide) (isomer mixture) | melting point 80 – 87 |
| 4-benzyloxymethyl-2,4-dimethyl-1,3-dioxolane-2-(N-(4-fluorophenyl)carboxamide) (isomer mixture) | melting point 52 – 77 |
| 4-benzyloxymethyl-2,4-dimethyl-1,3-dioxolane-2-(N-p-tolylcarboxamide) (isomer 1) | melting point 83 – 85 |
| 4-benzyloxymethyl-2,4-dimethyl-1,3-dioxolane-2-(N-p-tolylcarboxamide) (isomer 2) | melting point 67 – 70 |
| 4-benzyloxymethyl-2,4-dimethyl-1,3-dioxolane-2-(N-(4-methoxyphenyl)carboxamide (isomer 1) | melting point 96 – 98 |
| 4-benzyloxymethyl-2,4-dimethyl-1,3-dioxolane-2-(N-(4-methoxyphenyl)carboxamide (isomer 2) | melting point 79 – 81 |
| 4-benzyloxymethyl-2,4-dimethyl-1,3-dioxolane-2-(N-o-tolylcarboxamide) | R$_f$(CHCl$_3$) 0.55 |
| 4-benzyloxymethyl-2,4-dimethyl-1,3-dioxolane-2-(N-(2-chlorophenyl)carboxamide) | R$_f$(CHCl$_3$) 0.61 |
| 4-benzyloxymethyl-2,4-dimethyl-1,3-dioxolane-2-(N-(2-methoxyphenyl)carboxamide) | R$_f$(CHCl$_3$) 0.59 |
| 4-benzyloxymethyl-2,4-dimethyl-1,3-dioxolane-2-(N-(3-methoxyphenyl)carboxamide) | R$_f$(CHCl$_3$) 0.58 |
| 4-benzyloxymethyl-2,4-dimethyl-1,3-dioxolane-2-(N-m-tolylcarboxamide) | R$_f$(CHCl$_3$) 0.6 |
| 4-benzyloxymethyl-2,4-dimethyl-1,3-dioxolane-2-(N-(3-chlorophenyl)carboxamide) | R$_f$(CHCl$_3$) 0.6 |

EXAMPLE 8

Herbicidal Activity

To evaluate their herbicidal activity, the compounds of the invention were tested using as a representative range of plants: maize, Zea mays (Mz); rice, Oryza sativa (R); barnyard grass, Echinchloa crusgalli (BG); pea, Pisum sativum (P); linseed, Linum usitatissium (L); mustard, Sinapis alba (M); and sugar beet, Beta vulgaris (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz. soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilised, modified John Innes Compost mixture in which half the peat, by loose bulk, had been replaced by vermiculite.

The formulations used in the tests were prepared by diluting with water and solutions of the compounds in acetone containing 0.4% by weight of an alkylphenol-/ethylene oxide condensate available under the trade name Triton X-155. In the soil spray and foliar spray tests the acetone solutions were diluted with an equal volume of water and the resulting formulations applied to two dosage levels corresponding to 10 and 1 kilograms of active material per hectare respectively in a volume equivalent to 400 liters per hectare. In the soil drench tests one volume of the acetone solution was diluted for 155 volumes with water and the resulting formulation applied at one dosage level equivalent to 10 kilograms of active material per hectare in a volume equivalent to approximately 3,000 liters per hectare.

In the pre-emergence tests untreated sown soil and in the post-emergence tests untreated soil bearing seedling plants were used as controls.

The herbicidal effects of the compounds were assessed visually seven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

The results of the tests are set out in Table 2.

Table 2

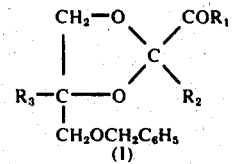
(I)

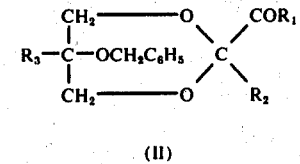
(II)

| Compound | | | | Dosage | Post-Emergence | | | | | | | | | | | | | | |
|---|---|---|---|---|---|---|---|---|---|---|---|---|---|---|---|---|---|---|---|
| | | | | | Soil Drench | | | | | | | Foliar Spray | | | | | | |
| Formula | $R_1$ | $R_2$ | $R_3$ | Kg/ha | $M_z$ | R | BG | P | L | M | SB | $M_z$ | R | BG | P | L | M | SB |
| I | $OC_2H_5$ | $CH_3$ | $CH_3$ | 10 | 4 | 0 | 6 | 0 | 0 | 2 | 0 | 3 | 0 | 8 | 1 | 9 | 9 | 7 |
| | | | | 1 | | | | | | | | 0 | 0 | 2 | 0 | 0 | 0 | 0 |
| I | OH | $CH_3$ | $CH_3$ | 10 | 0 | 0 | 0 | 0 | 0 | 0 | 0 | 1 | 0 | 5 | 1 | 6 | 5 | 1 |
| | | | | 1 | | | | | | | | 0 | 0 | 0 | 0 | 0 | 0 | 0 |
| I | $NHC_6H_5$ | $CH_3$ | $CH_3$ | 10 | — | — | — | — | — | — | — | 7 | 6 | 8 | 3 | 7 | 7 | 1 |
| | | | | 1 | | | | | | | | 3 | 1 | 7 | 3 | 6 | 4 | 0 |
| I | $NH_2$ | $CH_3$ | $CH_3$ | 10 | 6 | 3 | 5 | 2 | 1 | 3 | 0 | 2 | 4 | 7 | 7 | 8 | 9 | 5 |
| | | | | 1 | | | | | | | | 0 | 0 | 1 | 4 | 1 | 0 | 0 |
| I | $OC_2H_5$ | H | $CH_3$ | 10 | 0 | 0 | 0 | 0 | 0 | 0 | 0 | 1 | 1 | 8 | 2 | 7 | 6 | 0 |
| | | | | 1 | | | | | | | | 0 | 0 | 0 | 0 | 0 | 0 | 0 |
| II | $NHC_6H_5$ | $CH_3$ | $CH_3$ | 10 | — | — | — | — | — | — | — | 1 | 0 | 5 | 1 | 6 | 7 | 1 |
| | | | | 1 | | | | | | | | 0 | 0 | 0 | 0 | 1 | 0 | 0 |
| II | $OC_2H_5$ | $CH_3$ | $CH_3$ | 10 | 4 | 3 | 6 | 0 | 0 | 0 | 0 | 0 | 0 | 0 | 0 | 0 | 0 | 0 |
| | | | | 1 | | | | | | | | 0 | 0 | 0 | 0 | 0 | 0 | 0 |
| II | $NH_2$ | $CH_3$ | $CH_3$ | 10 | — | — | — | — | — | — | — | — | — | — | — | — | — | — |
| | | | | 1 | | | | | | | | | | | | | | |
| I | $NH(CH_2)_3CH_3$ | $CH_3$ | $CH_3$ | 10 | 6 | 4 | 7 | 0 | 0 | 3 | 0 | 6 | 2 | 7 | 2 | 8 | 9 | 3 |
| | | | | 1 | | | | | | | | 0 | 0 | 0 | 1 | 1 | 2 | 0 |
| I | NH(Cyclohexyl) | $CH_3$ | $CH_3$ | 10 | 0 | 0 | 3 | 0 | 0 | 0 | 0 | 1 | 3 | 8 | 3 | 8 | 9 | 4 |
| | | | | 1 | | | | | | | | 0 | 0 | 0 | 0 | 1 | 3 | 0 |
| I | $OC_2H_5$ | $CH_3$ | $C_2H_5$ | 10 | 1 | 1 | 0 | 0 | 1 | 1 | 1 | 3 | 2 | 7 | 5 | 8 | 8 | 6 |
| | | | | 1 | | | | | | | | 1 | 0 | 0 | 0 | 0 | 1 | 0 |
| I | $NHCH_2C_6H_5$ | $CH_3$ | $C_2H_5$ | 10 | 8 | 7 | 8 | 0 | 1 | 2 | 0 | 0 | 5 | 9 | 5 | 8 | 8 | 2 |
| | | | | 1 | | | | | | | | 1 | 0 | 1 | 0 | 1 | 4 | 1 |
| I | OH | $CH_3$ | $C_2H_5$ | 10 | 0 | 0 | 0 | 0 | 0 | 0 | 0 | 5 | 4 | 4 | 2 | 6 | 4 | 5 |
| | | | | 1 | | | | | | | | 0 | 0 | 0 | 0 | 0 | 0 | 0 |
| I | $NHC_6H_5$ (isomer 1) | $CH_3$ | $C_2H_5$ | 10 | 7 | 7 | 8 | 0 | 5 | 7 | 4 | 8 | 7 | 9 | 1 | 7 | 7 | 2 |
| | | | | 1 | | | | | | | | 7 | 4 | 8 | 0 | 6 | 5 | 1 |
| I | $NHC_6H_5$ (isomer 2) | $CH_3$ | $C_2H_5$ | 10 | 7 | 7 | 8 | 0 | 0 | 6 | 4 | 7 | 5 | 8 | 3 | 6 | 5 | 1 |
| | | | | 1 | | | | | | | | 0 | 0 | 0 | 0 | 0 | 0 | 0 |
| I | $OC_2H_5$ | $CH_3$ | $CH_2CH_2CH_3$ | 10 | 0 | 0 | 0 | 0 | 0 | 0 | 0 | 3 | 3 | 8 | 1 | 6 | 7 | 3 |
| | | | | 1 | | | | | | | | 0 | 0 | 0 | 0 | 0 | 0 | 0 |
| I | $NHC_6H_5$ (isomer 1) | $CH_3$ | $CH_2CH_2CH_3$ | 10 | 8 | 6 | 8 | 0 | 6 | 4 | 4 | 8 | 2 | — | 4 | 8 | 4 | 2 |
| | | | | 1 | | | | | | | | 7 | 0 | — | 4 | 7 | 3 | 1 |
| I | $NHCH_2C_6H_5$ | $CH_3$ | $CH_2CH_2CH_3$ | 10 | 5 | 0 | 4 | 0 | 0 | 0 | 0 | 6 | 7 | 8 | 1 | 6 | 5 | 5 |
| | | | | 1 | | | | | | | | 0 | 1 | 3 | 0 | 0 | 0 | 0 |
| I | NH(4-chloro-phenyl) | $CH_3$ | $CH_3$ | 10 | 8 | 3 | 8 | 0 | 5 | 0 | 0 | 7 | 0 | 8 | 3 | 6 | 3 | 1 |
| | | | | 1 | | | | | | | | 0 | 0 | 6 | 1 | 5 | 0 | 0 |
| I | NH(4-fluoro-phenyl) | $CH_3$ | $CH_3$ | 10 | 8 | 4 | 8 | 0 | 7 | 0 | 0 | 6 | 0 | 7 | 3 | 8 | 6 | 0 |
| | | | | 1 | | | | | | | | 2 | 0 | 6 | 0 | 6 | 0 | 0 |
| I | NH(p-tolyl) (isomer 1) | $CH_3$ | $CH_3$ | 10 | 1 | 0 | 6 | 0 | 0 | 0 | 0 | 3 | 3 | 6 | 1 | 7 | 2 | 1 |
| | | | | 1 | | | | | | | | 0 | 0 | 0 | 0 | 5 | 0 | 0 |
| I | NH(p-tolyl) (isomer 2) | $CH_3$ | $CH_3$ | 10 | — | — | — | — | — | — | — | — | — | — | — | — | — | — |
| | | | | 1 | | | | | | | | | | | | | | |
| I | NH(4-methoxyphenyl) (isomer mixture) | $CH_3$ | $CH_3$ | 10 | 8 | 3 | 8 | 4 | 7 | 2 | 0 | 8 | 3 | 8 | 3 | 7 | — | 0 |
| | | | | 1 | | | | | | | | 6 | 0 | 7 | 1 | 6 | 2 | 0 |
| I | NH(o-tolyl) | $CH_3$ | $CH_3$ | 10 | 7 | 6 | 7 | 0 | 6 | 0 | 0 | 7 | 4 | 8 | 5 | 6 | 8 | 1 |
| | | | | 1 | | | | | | | | 3 | 0 | 3 | 0 | 4 | 0 | 0 |
| I | NH(2-chlorophenyl) | $CH_3$ | $CH_3$ | 10 | 3 | 1 | 7 | 0 | 0 | 0 | 0 | 4 | 1 | 7 | 3 | 6 | 1 | 3 |
| | | | | 1 | | | | | | | | 0 | 0 | 2 | 0 | 5 | 0 | 2 |
| I | NH(2-methoxy-phenyl) | $CH_3$ | $CH_3$ | 10 | 8 | 3 | 7 | 0 | 2 | 0 | 0 | 6 | 1 | 7 | 3 | 7 | 3 | 4 |
| | | | | 1 | | | | | | | | 1 | 0 | 3 | 1 | 5 | 0 | 1 |
| I | NH(3-methoxy-phenyl) | $CH_3$ | $CH_3$ | 10 | 8 | 6 | 7 | 0 | 4 | 0 | 3 | 7 | 5 | 8 | 3 | 7 | 5 | 5 |
| | | | | 1 | | | | | | | | 4 | 0 | 7 | 1 | 5 | 1 | 3 |
| I | NH(m-tolyl) | $CH_3$ | $CH_3$ | 10 | 8 | 5 | 7 | 2 | 4 | 2 | 2 | 8 | 1 | 8 | 4 | 7 | 4 | 1 |
| | | | | 1 | | | | | | | | 7 | 0 | 7 | 2 | 5 | 0 | 0 |
| I | NH(3-chloro-phenyl) | $CH_3$ | $CH_3$ | 10 | 7 | 5 | 7 | 1 | 3 | 0 | 2 | 6 | 2 | 7 | 3 | 5 | 3 | 1 |
| | | | | 1 | | | | | | | | 1 | 0 | 6 | 1 | 4 | 1 | 0 |

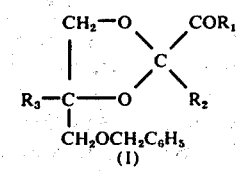
(I)

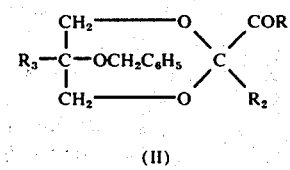
(II)

| Compound | | | | Dosage | Pre-Emergence | | | | | | |
|---|---|---|---|---|---|---|---|---|---|---|---|
| | | | | | Soil Spray | | | | | | |
| Formula | $R_1$ | $R_2$ | $R_3$ | Kg/ha | $M_z$ | R | BG | P | L | M | SB |
| I | $OC_2H_5$ | $CH_3$ | $CH_3$ | 10 | 7 | 9 | 9 | 0 | 1 | 0 | 0 |
| | | | | 1 | 1 | 0 | 8 | 0 | 0 | 0 | 0 |

3,986,860

Table 2-continued

| | | | | | | | | | | |
|---|---|---|---|---|---|---|---|---|---|---|
| I | OH | CH₃ | CH₃ | 10 | 0 | 3 | 4 | 0 | 0 | 4 | 0 |
| | | | | 1 | 0 | 0 | 0 | 0 | 0 | 0 | 0 |
| I | NHC₆H₅ | CH₃ | CH₃ | 10 | 8 | 9 | 9 | 8 | 7 | 6 | 0 |
| | | | | 1 | 5 | 8 | 9 | 6 | 6 | 5 | 0 |
| I | NH₂ | CH₃ | CH₃ | 10 | 1 | 5 | 9 | 8 | 4 | 5 | 0 |
| | | | | 1 | 0 | 0 | 9 | 7 | 2 | 3 | 0 |
| I | OC₂H₅ | H | CH₃ | 10 | 0 | 0 | 4 | 0 | 4 | 0 | 0 |
| | | | | 1 | 0 | 0 | 0 | 0 | 0 | 0 | 0 |
| II | NHC₆H₅ | CH₃ | CH₃ | 10 | 6 | 8 | 9 | 2 | 4 | 5 | 0 |
| | | | | 1 | 3 | 3 | 4 | 0 | 0 | 0 | 0 |
| II | OC₂H₅ | CH₃ | CH₃ | 10 | 8 | 9 | 9 | 4 | 6 | 6 | 1 |
| | | | | 1 | 1 | 8 | 8 | 0 | 1 | 2 | 0 |
| II | NH₂ | CH₃ | CH₃ | 10 | 3 | 1 | 7 | 0 | 2 | 4 | 1 |
| | | | | 1 | 0 | 0 | 1 | 0 | 0 | 0 | 0 |
| I | NH(CH₂)₃CH₃ | CH₃ | CH₃ | 10 | 9 | 8 | 9 | 3 | 6 | 5 | 5 |
| | | | | 1 | 0 | 0 | 8 | 0 | 0 | 0 | 0 |
| I | NH(Cyclohexyl) | CH₃ | CH₃ | 10 | 0 | 0 | 9 | 0 | 0 | 3 | 0 |
| | | | | | 0 | 0 | 0 | 0 | 0 | 0 | 0 |
| I | OC₂H₅ | CH₃ | C₂H₅ | 10 | 1 | 3 | 9 | 0 | 5 | 5 | 2 |
| | | | | 1 | 0 | 0 | 4 | 0 | 0 | 0 | 0 |
| I | NHCH₂C₆H₅ | CH₃ | CH₃ | 10 | 9 | 9 | 9 | 2 | 2 | 4 | 4 |
| | | | | 1 | 0 | 4 | 9 | 0 | 0 | 1 | 0 |
| I | OH | CH₃ | C₂H₅ | 10 | 2 | 4 | 7 | 3 | 4 | 8 | 4 |
| | | | | 1 | 0 | 1 | 2 | 0 | 0 | 1 | 0 |
| I | NHC₆H₅ (isomer 1) | CH₃ | C₂H₅ | 10 | 9 | 9 | 9 | 9 | 8 | 8 | 5 |
| | | | | 1 | 4 | 4 | 9 | 6 | 7 | 7 | 4 |
| I | NHC₆H₅ (isomer 2) | CH₃ | C₂H₅ | 10 | 6 | 4 | 9 | 8 | 8 | 8 | 5 |
| | | | | 1 | 1 | 1 | 9 | 4 | 4 | 3 | 1 |
| I | OC₂H₅ | CH₃ | CH₂CH₂CH₃ | 10 | 0 | 3 | 9 | 0 | 0 | 0 | 0 |
| | | | | 1 | 0 | 2 | 0 | 0 | 0 | 0 | 0 |
| I | NHC₆H₅ (isomer 1) | CH₃ | CH₂CH₂CH₃ | 10 | 9 | 9 | 9 | 9 | 8 | 8 | 6 |
| | | | | 1 | 7 | 9 | 9 | 2 | 0 | 7 | 5 |
| I | NHCH₂C₆H₅ | CH₃ | CH₂CH₂CH₃ | 10 | 7 | 7 | 9 | 4 | 5 | 4 | 0 |
| | | | | 1 | 3 | 2 | 9 | 1 | 0 | 0 | 0 |
| I | NH(4-chlorophenyl) | CH₃ | CH₃ | 10 | 7 | 7 | 9 | 7 | 7 | 7 | 0 |
| | | | | 1 | 0 | 4 | 9 | 0 | 3 | 4 | 0 |
| I | NH(4-fluorophenyl) | CH₃ | CH₃ | 10 | 9 | 9 | 9 | 9 | 7 | 8 | 1 |
| | | | | 1 | 8 | 9 | 9 | 2 | 6 | 6 | 0 |
| I | NH(p-tolyl) (isomer 1) | CH₃ | CH₃ | 10 | 5 | 8 | 9 | 1 | 6 | 5 | 0 |
| | | | | 1 | 4 | 5 | 9 | 0 | 0 | 2 | 0 |
| I | NH(p-tolyl) (isomer 2) | CH₃ | CH₃ | 10 | 9 | 9 | 9 | 9 | 8 | 8 | 2 |
| | | | | 1 | — | — | — | — | — | — | — |
| I | NH(4-methoxyphenyl) (isomer mixture) | CH₃ | CH₃ | 10 | 9 | 9 | 9 | 9 | 7 | 8 | 0 |
| | | | | 1 | 8 | 9 | 9 | 6 | 7 | 5 | 0 |
| I | NH(o-tolyl) | CH₃ | CH₃ | 10 | 9 | 9 | 9 | 0 | 5 | 6 | 0 |
| | | | | 1 | 6 | 9 | 9 | 0 | 1 | 2 | 0 |
| I | NH(2-chlorophenyl) | CH₃ | CH₃ | 10 | 4 | 9 | 9 | 0 | 6 | 5 | 0 |
| | | | | 1 | 2 | 9 | 9 | 0 | 0 | 5 | 0 |
| I | NH(2-methoxyphenyl) | CH₃ | CH₃ | 10 | 9 | 9 | 9 | 8 | 8 | 7 | 6 |
| | | | | 1 | 5 | 9 | 9 | 0 | 0 | 5 | 0 |
| I | NH(3-methoxyphenyl) | CH₃ | CH₃ | 10 | 9 | 9 | 9 | 7 | 8 | 7 | 5 |
| | | | | 1 | 9 | 9 | 9 | 3 | 5 | 7 | 3 |
| I | NH(m-tolyl) | CH₃ | CH₃ | 10 | 9 | 9 | 9 | 8 | 7 | 7 | 5 |
| | | | | 1 | 7 | 9 | 9 | 7 | 7 | 7 | 2 |
| I | NH(3-chlorophenyl) | CH₃ | CH₃ | 10 | 8 | 9 | 9 | 7 | 7 | 6 | 4 |
| | | | | 1 | 4 | 9 | 9 | 1 | 6 | 6 | 3 |

We claim as our invention:

1. A herbicidal composition comprising a cyclic acetal derivative of the formula

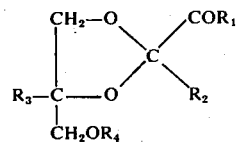

wherein $R_1$ is hydroxy, alkoxy of 1 to 6 carbon atoms or a group —NHZ in which Z is hydrogen, alkyl of up to 6 carbon atoms, cyclohexyl, benzyl, phenyl-amino, phenyl or phenyl substituted by a fluorine atom, by one or two chlorine atoms, by one or two methyl groups or by methoxy; $R_2$ is a hydrogen atom or alkyl of 1 to 6 carbon atoms; $R_3$ is alkyl of 1 to 6 carbon atoms; and $R_4$ is benzyl.

2. The method of controlling unwanted plant growth at a locus which comprises applying to the locus a cyclic acetal derivative as shown in claim 1.

3. A composition as claimed in claim 1 wherein $R_1$ is hydroxy, ethoxy or a group of the formula —NHZ in which z is hydrogen or butyl, cyclohexyl, benzyl, phenylamino, phenyl, fluorophenyl, chlorophenyl, dichlorophenyl, tolyl, dimethylphenyl, or methoxyphenyl; $R_2$ is hydrogen or methyl, $R_3$ is methyl, ethyl or propyl; and $R_4$ is benzyl.

4. A composition as claimed in claim 3 wherein $R_1$ is —NHZ is which Z is phenyl, and $R_2$ is methyl.

5. A composition as claimed in claim 4 wherein $R_3$ is ethyl.

6. A composition as claimed in claim 3 wherein $R_1$ is N-(4-fluorophenyl).

7. A composition as claimed in claim 3 wherein $R_1$ is N-(4-methoxyphenyl).

8. A composition as claimed in claim 3 wherein $R_1$ is N-(2-methylphenyl).

* * * * *